United States Patent
Cecchi et al.

(10) Patent No.: US 6,448,069 B1
(45) Date of Patent: Sep. 10, 2002

(54) EMBRYO-CULTURING APPARATUS AND METHOD

(75) Inventors: Michael D. Cecchi, Madison, CT (US); Jacques Cohen, Mountain Lakes; Timothy Schimmel, Randolph, both of NJ (US)

(73) Assignee: GenX International Corp., Guilford, CT (US)

( * ) Notice: Subject to any disclaimer, the term of this patent is extended or adjusted under 35 U.S.C. 154(b) by 132 days.

(21) Appl. No.: 09/590,389

(22) Filed: Jun. 9, 2000

(51) Int. Cl.$^7$ ............................................... C12M 3/00

(52) U.S. Cl. .................. 435/305.2; 435/29; 435/366; 435/373; 435/288.5; 435/297.5

(58) Field of Search ................................ 435/366, 373, 435/288.4, 288.5, 374, 297.5, 305.2, 305.3, 29, 325

(56) References Cited

U.S. PATENT DOCUMENTS 5,578,490 A * 11/1996 Martinez Ubeira
5,891,712 A * 4/1999 May
6,193,647 B1 * 2/2001 Beebe et al.

* cited by examiner

*Primary Examiner*—William H. Beisner
(74) *Attorney, Agent, or Firm*—William W. Jones

(57) ABSTRACT

An embryo culturing method and apparatus enables a plurality of embryos to be grown in communal clusters in a culturing container. The embryos are kept separate from each other in open interconnected compartments that are disposed in the culture container. Each compartment is contained in a structure having a plurality of interconnected compartments, and each compartment is sized to contain a single embryo. The culturing container will contain a plurality of the compartmentalized structures. The method and apparatus of this invention includes a culturing container, such as a Petrie dish, in which the embryos are grown. The Petrie dish preferably contains a plurality of the embryo-culturing compartmentalized structures which can be positioned in the Petrie dish in a predetermined pattern. For example, the compartmentalized structuress can be positioned in the Petrie dish at the 12 O'Clock, 2 O'Clock, 4 O'Clock, 8 O'Clock and 10 O'clock positions, or in any other planned deployment. The individual structures can be individually identified by letters, for example, such as A, B, C, D, etc. Each compartmentalized structure can contain a plurlaity, for example four, compartments which are interconnected for fluid exchange, but which are sized to restrain migration of an embryo from one compartment to another. The compartments in each structure can be identified by numerals, i.,e., 1, 2, 3 and 4. Thus each compartment in each structure would have a unique identifier code, such as A1, B2, C3, and the like; or 1-4, 5-8, 9-12, or the like. Any identifier system can be used which will enable the individual embryos to be distinguished one from another. After the embryos are placed in the compartments in each structure, each of the structures is covered with a drop of an embryo-enhancing growth nutrient so that each of the embryos in any one structure is exposed to a common growth nutrient, and each embryo in each compartmentalized structure can share growth by-products with each of the other embryos in the same compartmentalized structure.

21 Claims, 3 Drawing Sheets

EMBRYO-CULTURING APPARATUS AND METHOD

TECHNICAL FIELD

This invention relates to a method and apparatus for culturing or growing individually identifiable embryos in a communal environment. More specifically, this invention relates to an embryo culturing apparatus and method wherein individual embryos in the apparatus are kept physically separated from each other, but are permitted to share a common growth-enhancing nutrient, and each other's growth by-products, thereby resulting in an increased proficiency of the embryo growth process.

BACKGROUND ART

Human, and other animal embryos, are presently grown in a suitable growth-enhancing nutrient, typically for about three days, prior to implantation of the embryos into a female's reproductive system. There are several generally practiced embryo growth procedures which are presently in use. One of the generally practiced embryo growth techniques involves the use of a culturing container, such as a Petrie dish, in which individual embryos are placed in spaced-apart locations in the culturing dish. This technique involves the placement of individual embryos on a growth-enhancing nutrient in spaced apart positions in the Petrie dish, and subsequently immersing each of the individual embryos in a drop of a growth-enhancing nutrient. In this manner, the individual embryos are kept separate from each other and can be easily identified, one from another, and separately examined. Thus, the advantage of this procedure is the ability to monitor each individual embryo throughout the growth period so that there is a degree of selectivity available at the uterine-implanting stage of the process. One drawback in using this procedure relates to the fact that embryonic growth seems to be improved when the several embryos being grown are grown in a common growth-enhancing nutrient and are able to share each other's growth induced by-products.

Another of the generally practiced embryo growth techniques involves clustering a plurality of embryos together on a Petrie dish or in a growth tube, and covering the cluster with a common drop of the growth-enhancing nutrient. Using this technique, all of the embryos in a cluster are exposed to the same growth-enhancing nutrient drop and are able to share that growth-enhancing nutrient and also share their respective by-products of the growth process. The drawback with the second technique is that one cannot distinguish one embryo from another in the cluster, in other words, each individual embryo cannot be separately monitored during the growth process. Thus, the ability to select a preferred one of the grown embryos for implanting is somewhat impaired by use of the second growth technique.

It would be highly desirable to provide an embryo growing method and apparatus, which would provide the ability to segregate the individual embryos, one from another, while also providing the ability to allow the segregated embryos to share a common growth-enhancing nutrient and share each other's growth by-products.

DISCLOSURE OF THE INVENTION

This invention relates to an improved method and apparatus for growing embryos in vitro prior to implantation of the embryo in a female's reproductive system. The method and apparatus of this invention provides for the positive identification of each of the embryos being grown, and also allows several embryos to share a common growth-enhancing nutrient solution, and to share each other's growth by-products. Thus embryos can be individually monitored as to their growth and development. The growth process is performed in a container, such as a Petrie dish, or the like. A plurality of compartmentalized embryo-containing structures are dispersed in the Petrie dish in a predetermined pattern. Each of the compartmentalized structures contains a plurality of separate compartments which are sized to hold one embryo each. The compartments are separated from each other by pickets which form a fence-like barrier between each embryo compartment in each of the compartmentalized structures. Each of the compartmentalized structures thus allows inter compartmental migration of the growth-enhancing nutrient and of growth by-products produced by each of the embryos disposed in one of the structures. The compartmentalized structures are also sized so as to be submersible in a single drop of the embryo growth-enhancing nutrient. The compartmentalized structures are preferably molded into and are integral with the bottom wall of the Petrie dish, which in turn is molded from a suitable plastic material. The plastics preferred are plastics which exhibit minimal off gassing of their structural compounds.

The following is a general description of one manner of using the apparatus of this invention for in vitro growing of fertilized embryos prior to implantation of an embryo into a female recipient's reproductive tract. As noted above, the compartmentalized embryo-containing structures are preferably positioned in the Petrie dish in some predetermined location. In such an arrangement there will be a plurality of the compartmentalized structures in the Petrie dish. These compartmentalized structures can be visibly designated by the letters A, B, C, D, etc., and of course their locations on the Petrie dish will be known and fixed. An area on the Petrie dish can be utilized to display embryo recipient and embryo growth information for a technician monitoring the growth of the embryos in the apparatus. Each of the compartmentalized structures will include a plurality of compartments, say, for example, four compartments. Each compartment in each compartmentalized structure can be designated by a numeral, such as 1, 2, 3, 4, and the like. With such an apparatus, there will be a plurality of different compartments, each of which will contain a separate embryo. Each of the compartments can be uniquely identified as, for example, A1, B2, C3, and the like. Thus, there could be A1–A4 embryo compartments, B1–B4 embryo compartments, and the like, in the Petrie dish. With the apparatus of this invention, the growth history of each of the embryos can be monitored, and the embryo growth history can be recorded in individual embryo growth histograms by a technician monitoring embryo growth in the apparatus. The specific number of the plurality of individual compartments in the compartmentalized embryo-growth structure can vary, as required. By monitoring individual embryo growth history, the best embryonic candidate for implantation, from the group of embryos being grown in the apparatus, can be identified. The individual embryos may be studied and monitored as to their morphological development and viability during the growth term in the assembly. Information regarding morphological development and viability for each of the individual embryos in the compartments can be documented for future individual embryo viability determinations.

The following is a listing of several desirable, but nonessential, objects of this invention.

It is an object of this invention to provide an improved embryo growth-supporting method and apparatus which enables one to monitor the growth of individual embryos which are disposed in a growth-enhancing nutrient.

It is another object of this invention to provide a method and apparatus of the character described which enables individual embryos in the growth-enhancing nutrient to share growth by-products of other embryos in the growth-enhancing nutrient.

It is a further object of this invention to provide an apparatus of the character described which can be easily and inexpensively manufactured.

It is another object of this invention to provide a method and apparatus of the character described wherein individual embryos in the apparatus can be cataloged with specific identification indicia which can be used to indicate the exact location of each of the embryos in the apparatus, and their individual growth history.

BRIEF DESCRIPTION OF THE DRAWINGS

These and other objects and advantages of the invention will become more readily apparent from the following detailed description of an of the invention, when taken in conjunction with the accompanying drawings in which.

DETAILED DESCRIPTION OF SPECIFIC EMBODIMENTS OF THE INVENTION

Figure 1:
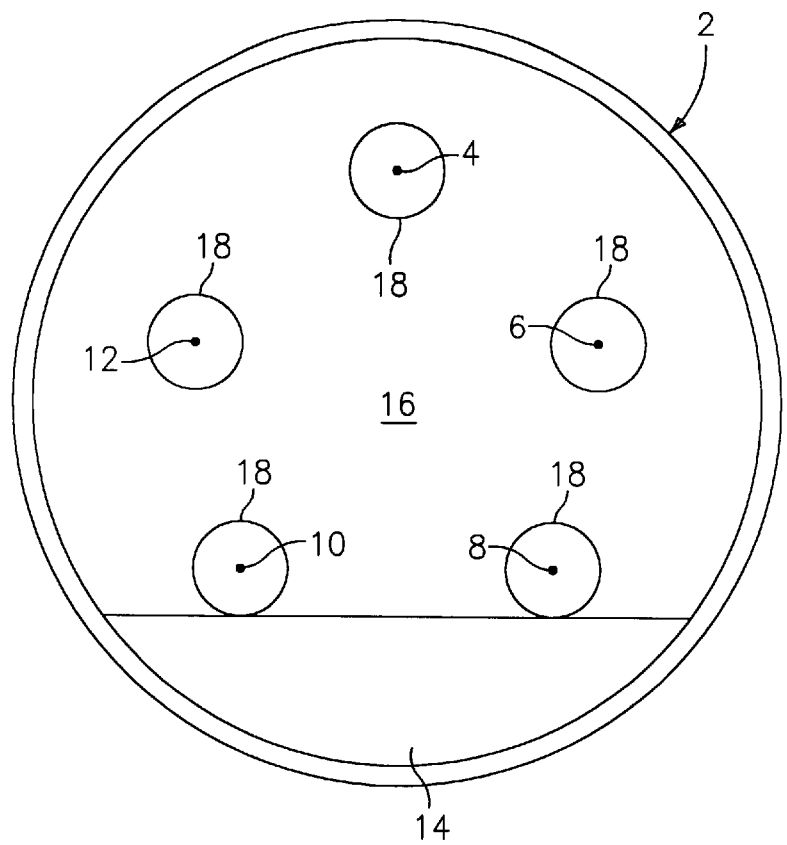
FIG. 1 is a plan view of an embryo growth container formed in accordance with this invention which includes five compartmentalized embryo growth structures.

Referring now to the drawings, FIG. 1 is a top plan view of an embryo growth container, denoted generally by the numeral 2, which is formed in accordance with this invention. The container 2 includes a plurality of compartmentalized embryo-growth structures 4, 6, 8, 10 and 12. The structures 4, 6, 8, 10 and 12 are preferably formed as integral components of the container 2, and details of their construction are set forth below. The container 2 also includes an area 14 on which information relating to the embryos, such as recipient; time in place; growth-enhancing nutrient; etc. can be written. The container 2 is preferably a Petrie dish-like device which is formed from a suitable material, such as polystyrene, acrylics, poly carbonates, TEFLON®, glass, or the like suitable materials, and the structures 4, 6, 8, 10 and 12 are preferably integrally molded extensions of the bottom wall 16 of the container 2. When embryos are being grown in the apparatus, each of the structures 4, 6, 8, 10 and 12 will be immersed in separate drops 18 of a growth-enhancing nutrient, such as an isotonic growth medium which consists of, or is equivalent to, mammalian tubal fluid; a solution comprising vitamins, amino acids, proteins, or the like; or other culture media which will support growth of the embryos. Obviously, the choice of a specific culture media will depend on the type of embryos being cultured.

Figure 2:
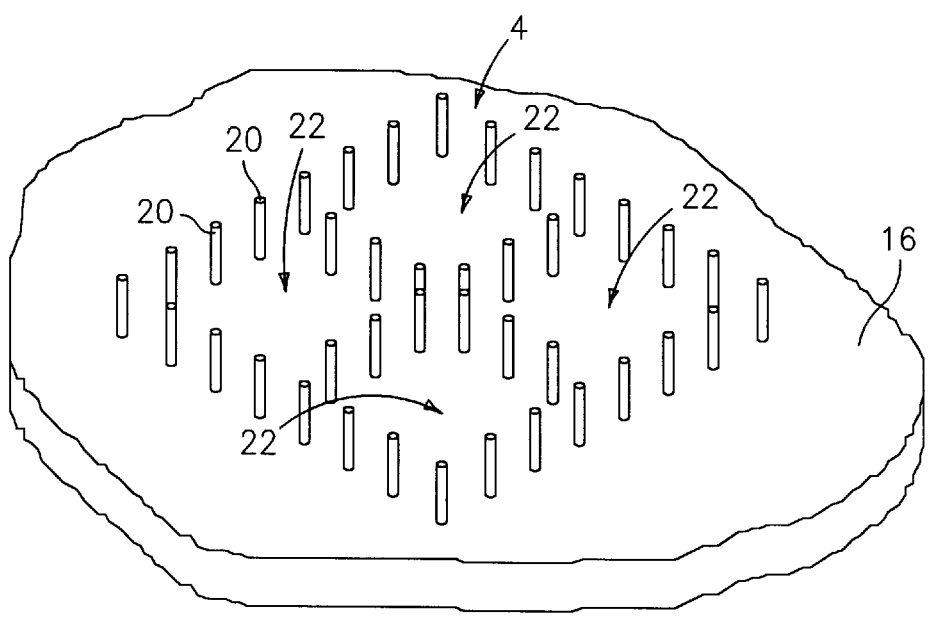
FIG. 2 is an enlarged fragmented perspective view of one of the compartmentalized embryo growth structures in the container of FIG. 1.

Referring now to FIG. 2, details of one of the structures 4, 6, 8, 10 or 12 are shown. Each of the structures 4–12 includes a plurality of spaced-apart pickets 20 which, in the embodiment shown, combine to form four compartments 22. The pickets 20 serve to form liquid-permeable barriers between adjacent compartments 22, and also between the compartments and the surrounding growth-enhancing nutrient 18. Each of the compartments 22 is sized to received a single fertilized embryo 24 (See FIG. 4) which is to be grown in the container 2 for a period of up to about five days, or for a period as short as three days. The length of the incubation time is such that the likelihood of embryo viability after implantation is more accurately assessable. Thus, each compartmentalized structure 4–12 can contain four separate individual embryos, if need be.

Figure 3:
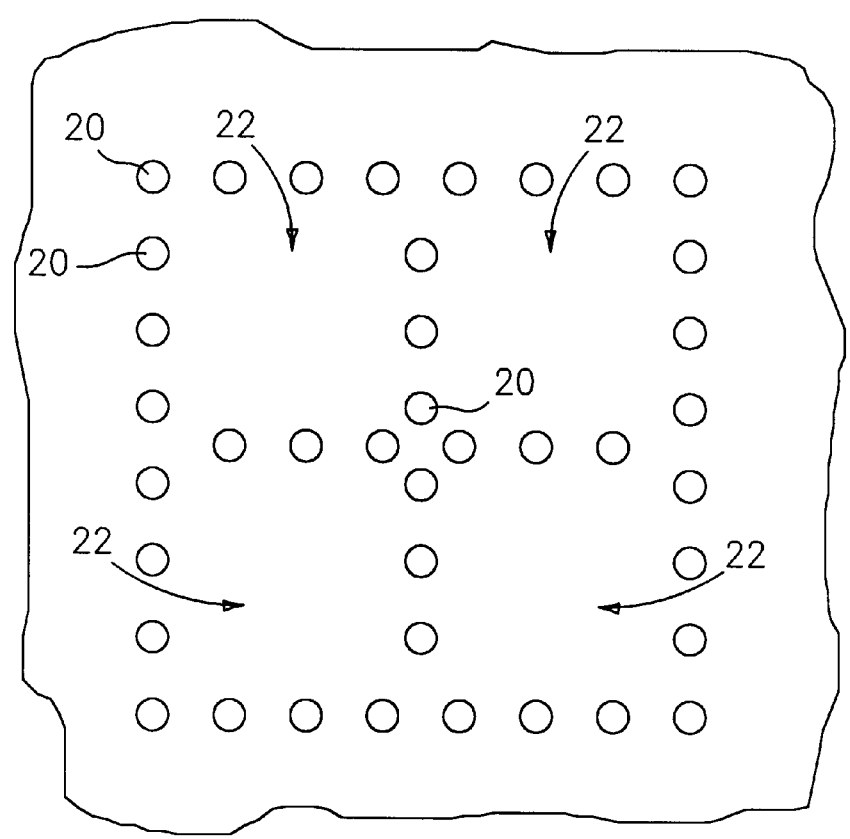
FIG. 3 is a plan view of one of the compartmentalized embryo growth structures.

FIG. 3 is a magnified plan view of one of the structures 4–12 showing one preferred sizing of the compartments 22; the spacing between adjacent pickets 20; the thickness of each of the pickets 20; and the peripheral dimensions of each of the entire structures 4–12. It will be appreciated that each of the structures 4–12 will preferably be identical in size. The primary purpose of the structures 4–12 is simply to allow individual embryos to be grown or cultured in a communal environment so that they can share the same growth-enhancing nutrient and can share growth by-products, while allowing each of the embryos to be separately categorized and monitored. The structures 4–12 also are operable to stabilize the position of each of the drops 18 of culture media in the container 2.

The following dimensions of various features of the structures 4–12 are exemplary of one embodiment of an apparatus 2 which is suitable for growing human embryos prior to implantation in a female recipient. In an assembly suitable for use in culturing human embryos, the pickets 20 have a typical thickness of about 0.010 in.; and a typical height of about 0.002 in. The spaces between adjacent ones of the peripheral pickets is typically about 0.0043 in.; and between the inner pickets are about 0.0033 in. The inner width of each of the compartments 22 is typically about 0.040 in.; and the total outer width of each of the structures 4 is typically about 0.110 in. Human embryos are generally spherical in shape and have a typical initial diameter of about 0.0044 in. and may grow to an implantation diameter of between 0.0130 in. to about 0.0200 in., depending on the length of time the culturing procedure is carried on.

It will be appreciated that the sizes of the embryos will vary depending on what type of mammalian embryos are being grown. Some species will have larger embryos than humans, and other species will have smaller embryos than humans. It will be apparent that the individual compartments 22 should be large enough to provide room for growth of the embryos, and the pickets 20 must be high enough merely to prevent the embryos from being accidentally displaced from the compartments, and also preferably to stabilize the position of the culture media drops 18. The compartments 22 are all open at their tops, and have liquid permeable sides. Each of the embryos disposed in the container 2 can be visually monitored under appropriate magnification.

Figure 4:
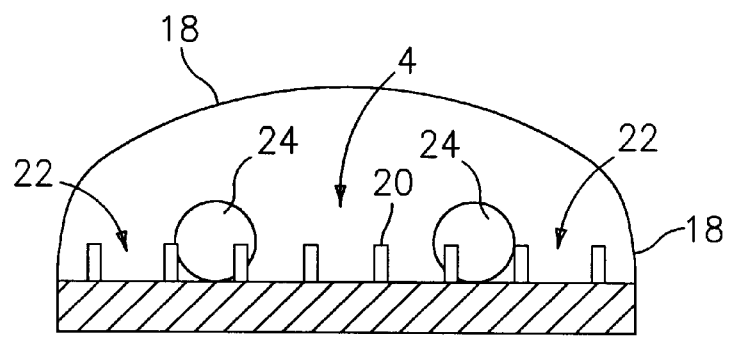
FIG. 4 is a side elevational view of one of the compartmentalized embryo growth structures showing an embryo in each compartment in the structure.

FIG. 4 shows schematically how each of the embryos 24 resides in a respective one of the different compartments 22, how the embryos are passively constrained in the compartments 22; and how a single drop 18 of a culturing medium can cover an entire structure and its contents.

Figure 5:
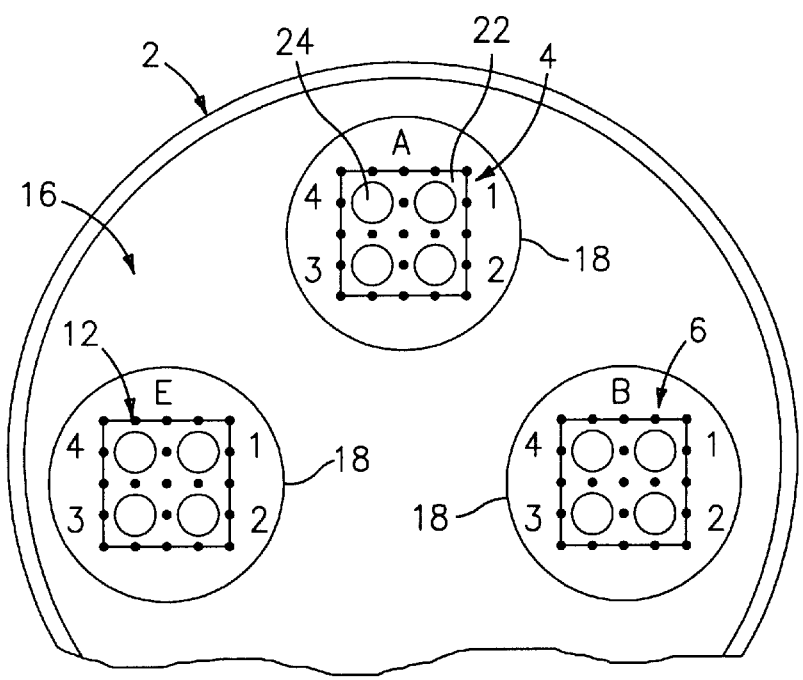
FIG. 5 is a fragmented plan view of a portion of the embryo growth container showing the compartmentalized embryo-growth structures, magnified in size, and showing the manner in which individual embryos can be cataloged and individually identified in the apparatus.

FIG. 5 is a fragmented schematic view of a portion of the container 2, with three of the structures 4, 6 and 12 being magnified in size, so as to be somewhat similar to what would be visually observed under magnification. FIG. 5 illustrates how each of the compartments 22 can be assigned a unique two bit cataloging code. In that manner, each of the embryos 24 in the container 2 can also be assigned a unique two bit catalog code. One operative cataloging approach would be to assign different letters to each of the structures 4–12, thus structure 4 could be "A"; structure 6 could be "B"; and so on to structure 12, which could be "E". These structure-identifying letters could be engraved, or otherwise applied to the bottom wall 16 of the container 14, as shown in FIG. 5. Additionally, the individual compartments 22 could be assigned different numbers, such as "1", "2", "3", "4", and the like. These numbers could also be engraved or otherwise applied to the bottom wall 16 of the container 14, as shown in FIG. 5. Using such an approach, each of the compartments 22 would be assigned a unique catalog code, such as "A1", "B2", "D4", and the like. In this manner, any embryo 24 in the container 2 of particular interest can be located and observed. Alternatively, a simple series of numbers or letters could be used to identify the compartments 22 and distinguish one from another.

Figure 6:
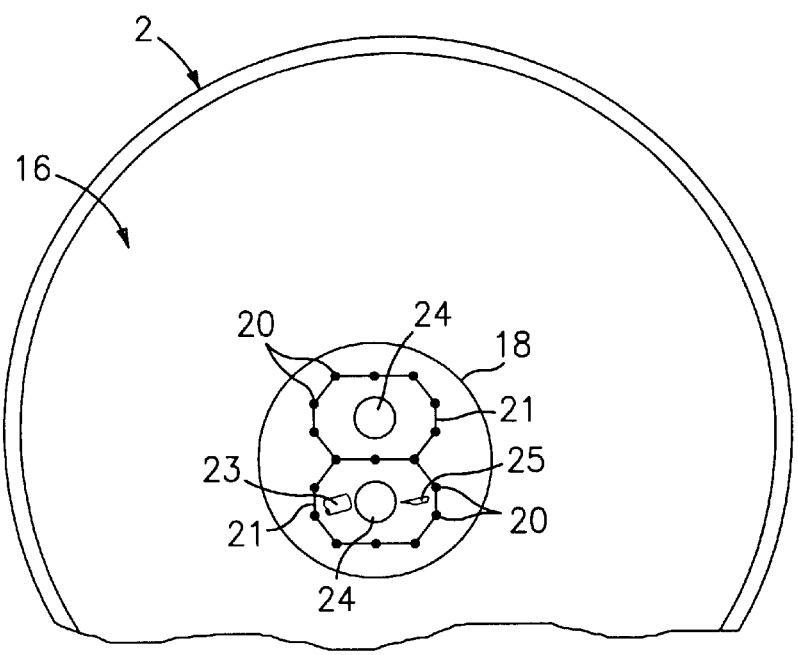
FIG. 6 is a view similar to FIG. 5 but showing a different geometric configuration of the compartments in the container.

Referring now to FIG. 6, the pickets 20 are arranged in a oval array and the ova 24 is positioned essentially in the center of the array of pickets 20. The embodiment shown in FIG. 6 indicates that there can be a number of adjacent oval arrays of the pickets 20, all of which are covered by a drop of the growth-enhancing nutrient 18. The pickets 20 may be wrapped in a "fence" of a liquid-permeable membrane 21. The membrane 21 may also be employed in the embodiments shown in FIG. 5. Use of the membranes 21 is not, however, a necessary requirement for practicing the invention disclosed herein. As shown in FIG. 6, the use of the oval or laterally elongated "corrals" for containing the ova 24 allows room in the corrals for one to insert micro-tools such as a pipette 23 and a syringe 25 into the corrals for use in manipulating the embryos 24. The pipette 23 can be used to securely position the embryos 24 in the corral, and the syringe 25 can be used to fertilize the embryo 24. Obviously, the increased area of each corral allows the use of other micro-tools to manipulate the embryos 24.

It will be readily appreciated that the apparatus and method of this invention enable the growth and culturing of a plurality of separate embryos with a common culture medium, while allowing each of the embryos to share other embryos' growth by-products. Each of the embryos being grown in the apparatus can be individually monitored, identified, and cataloged. Growth monitoring is performed by visually observing the morphology of the individual embryos during the culturing period. The individual embryos are passively kept physically separate from each other, while allowing communal growth of the embryos. The culture medium's location in the growth container is also stabilized so that it does not drift about in the container. The use of asymmetric increased area compartments in the culturing container allows the embryos to be individually treated or modified with the use of embryo-specific micro-tools.

Since many changes and variations of the disclosed embodiment of the invention may be made without departing from the inventive concept, it is not intended to limit the invention except as required by the appended claims.

What is claimed is:

1. An embryo-culturing apparatus comprising:
   a) a container for holding embryos, and for holding a culturing medium which supports growth of the embryos, said container having a bottom wall; and
   b) at least one compartmentalized structure in said container, said structure being positioned on said bottom wall of said container, and said structure including at least four compartments which are sized for receiving individual embryos, each of said compartments in a structure being interconnected so as to allow inter-compartmental fluid migration, while at the same time, being operable to prevent inter-compartmental embryo migration within a structure.

2. The embryo culturing apparatus of claim 1 wherein each compartment in a structure is bounded by spaced-apart pickets projecting upwardly from said bottom wall of said container.

3. The embryo culturing apparatus of claim 2 wherein said pickets are integral with said bottom wall of said container.

4. The embryo culturing apparatus of claim 2 wherein said pickets are spaced apart and sized so as to contain and restrict inter-compartmental migration of human embryos.

5. The embryo culturing apparatus of claim 1 wherein each compartment in a structure is identified by a unique indicia or indicium which is displayed on said container bottom wall in close proximity with the respective identified compartments so that an embryo in each compartment can be individually monitored during an embryo culturing process.

6. The embryo culturing apparatus of claim 1 wherein each compartment in a structure is bounded by spaced-apart pickets projecting from said container bottom wall, which pickets are operable to stabilize the position of culturing medium on said container bottom wall.

7. The embryo culturing apparatus of claim 1 wherein said container bottom wall includes an area wherein embryo identification and growth information can be inscribed.

8. The embryo culturing apparatus of claim 1 wherein each compartment in a structure is bounded by a fluid permeable membrane.

9. The embryo culturing apparatus of claim 1 wherein each compartment in a structure is laterally expanded so as to allow access of micro-tools into said compartments to enable manipulation of individual embryos in said compartments.

10. An embryo culturing assembly comprising:
    a) a container for holding embryos, and for holding a culturing medium which supports growth of the embryos, said container having a bottom wall;
    b) at least one compartmentalized structure in said container, said structure being positioned on said bottom wall of said container, and said structure including a plurality of compartments which are sized for receiving individual embryos, each of said compartments in a structure being interconnected so as to allow inter-compartmental fluid migration, while at the same time, being operable to prevent inter-compartmental embryo migration within a structure;
    c) an individual fertilized mammalian embryo disposed in at least two of said compartments in a structure; and
    d) respective individual drops of a culture medium disposed on said container bottom wall, said individual culture medium drops covering all embryos disposed in respective individual structures, whereby there are individual culture medium drops covering all of the embryos in individual structures.

11. The embryo culturing assembly of claim 10 wherein said culture medium is a medium selected from the group consisting of mammalian tubal fluid; a medium equivalent to mammalian tubal fluid; solutions of vitamins, amino acids and proteins; and other isotonic growth media; and mixtures thereof.

12. The embryo culturing assembly of claim 10 wherein each compartment in a structure is bounded by spaced-apart pickets projecting upwardly from said bottom wall of said container.

13. The embryo culturing assembly of claim 12 wherein said pickets are integral with said bottom wall of said container.

14. The embryo culturing assembly of claim 12 wherein said pickets are spaced apart and sized so as to contain and restrict inter-compartmental migration of human embryos.

15. The embryo culturing assembly of claim 10 wherein each compartment in a structure is identified by a unique indicia or indicium displayed on said container bottom wall in close proximity with the respective identified compartments so that an embryo in each compartment can be individually monitored during an embryo culturing process.

16. The embryo culturing assembly of claims 10 wherein each compartment in a structure is bounded by spaced-apart pickets projecting from said container bottom wall, which pickets are operable to stabilize the position of culturing medium on said container bottom wall.

17. The embryo culturing assembly of claim 10 wherein said container bottom wall includes an area wherein embryo identification and growth information can be inscribed.

18. The embryo culturing assembly of claim 10 wherein there are four embryo compartments in each structure in said container.

19. A method for performing an embryo growth culturing process, said method comprising:
  a) the step of providing a container for holding embryos, and for holding a culturing medium which supports growth of the embryos, said container having a bottom wall;
  b) the step of providing at least one compartmentalized structure in said container, said structure being positioned on said bottom wall of said container, and said structure including a plurality of compartments-which are sized for receiving individual embryos, each of said compartments in a structure being interconnected so as to allow inter-compartmental fluid migration, while at the same time, being operable to prevent inter-compartmental embryo migration within a structure;
  c) the step of placing a single embryo in more than one of said compartments in said structure so as to form a plurality of compartmentalized embryos in said container;
  d) the step of immersing each structure which contains compartmentalized embryos with a drop of an embryo culturing medium so as to form a plurality of immersed embryos in said container; and
  e) the step of monitoring growth of each of said immersed embryos over a period of time needed to determine uterine implant viability of each of said immersed embryos.

20. The method of claim 19 further comprising the step of providing a unique visible cataloging indicium for each of said immersed embryos whereby each of said immersed embryos are individually distinguishable from other immersed embryos, and whereby growth information for each of said immersed embryos can be individually recorded.

21. The method of claim 19 wherein said monitoring step involves visually observing morphological development of each of said immersed embryos and recording such observations.

* * * * *